US00PP21419P2

(12) United States Plant Patent
Bergman

(10) Patent No.: US PP21,419 P2
(45) Date of Patent: Oct. 26, 2010

(54) ***CHRYSANTHEMUM* PLANT NAMED 'BOLD YONEW YORK'**

(50) Latin Name: *Chrysanthemum×morifolium*
Varietal Denomination: Bold Yonew York

(75) Inventor: Wendy R. Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,654

(22) Filed: Sep. 25, 2009

(51) Int. Cl.
*A01H 5/00* (2006.01)

(52) U.S. Cl. ..... Plt./286

(58) Field of Classification Search ..... Plt./286
See application file for complete search history.

*Primary Examiner*—Annette H Para
(74) *Attorney, Agent, or Firm*—S. Matthew Edwards

(57) ABSTRACT

A new *Chrysanthemum* plant named 'Bold Yonew York,' particularly distinguished by the decorative flower form with bold red-purple colored immature ray florets and pink mature ray florets, uniform spreading habit and flowering response, and good shelf life.

1 Drawing Sheet

Latin name of the genus and species of the plant claimed: *Chrysanthemum×morifolium.*

Varietal denomination. 'Bold Yonew York'.

BACKGROUND OF THE NEW PLANT

The present invention comprises a new *Chrysanthemum*, botanically known as *Chrysanthemum×morifolium*, and hereinafter referred to by the variety name 'Bold Yonew York'.

'Bold Yonew York' is a product of a planned breeding program. The new cultivar has decorative flower form with bold red-purple colored immature ray florets and pink mature ray florets, uniform spreading habit and flowering response, and good shelf life.

'Bold Yonew York' originates as a natural whole plant mutation of 'Yonew York,' U.S. Plant Pat. No. 15,698. 'Bold Yonew York' was discovered and selected by the inventor as a single flowering plant within a population of the parent cultivar grown outdoors in a field covered by saran in Fort Myers, Fla., in December 2006. The parent cultivar 'Yonew York' has lighter pink colored ray florets, a little shorter plant habit, and the whole plant matures a little faster.

The first act of asexual reproduction of 'Bold Yonew York' was accomplished when vegetative cuttings were propagated from the initial selection in March 2007, in a controlled environment in Fort Myers, Fla.

A Plant Breeder's Right for this cultivar was applied for in Canada in March 2009. 'Bold Yonew York' has not been made publicly available more than one year prior to the filing of this application.

BRIEF SUMMARY OF INVENTION

Horticultural examination of plants grown from cuttings of the plant initiated in March 2007, and continuing thereafter, has demonstrated that the combination of characteristics as herein disclosed for 'Bold Yonew York' are firmly fixed and are retained through successive generations of asexual reproduction.

'Bold Yonew York' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Bold Yonew York' with colors being as true as possible with an illustration of this type. The photographic drawing shows four flowering potted plants of the new variety growing in a five inch pot, and a close-up of the flowers.

DETAILED BOTANICAL DESCRIPTION

The plant descriptions, measurements and aforementioned photographs were taken in Gilroy, Calif. in April 2009 under greenhouse conditions. These plants were started and grown in central coastal California, then shipped to Gilroy, Calif. in April 2009. Plants were grown under conditions which approximate those generally used in commercial potted *chrysanthemum* production and were about 9 weeks of age.

Color references are made to The Royal Horticultural Society Colour Chart (R.H.S.) 2001.

TABLE 1

DIFFERENCES BETWEEN THE NEW VARIETY 'BOLD YONEW YORK' AND A SIMILAR VARIETY

| | 'Bold Yonew York' | 'Yopresidio' (U.S. Plant Pat. No. 13,896) |
|---|---|---|
| Plant habit size: | Shorter, more spreading | Taller, less spreading |
| Flower size: | Smaller | Larger |
| Flower color: | Generally more purple-pink | Generally more red-pink |

Plant:
*Form, growth and habit.*—Herbaceous pot-type; upright and somewhat spreading, freely branching. Suitable for production-center budded or no bud removal.
*Plant height.*—25-30 cm.
*Plant height (inflorescence included).*—30-34 cm.
*Plant width.*—16-20 cm.
Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—RHS 137A.
*Lower surface.*—Closest to RHS 147B.
*Mature, leaf color, upper surface.*—RHS 137A.
*Lower surface.*—Closest to RHS 147B.
*Length.*—8-8.5 cm.
*Width.*—6-6.5 cm.
*Shape.*—Ovate.
*Base shape.*—Acuminate.
*Apex shape.*—Abruptly acute.
*Margin.*—Palmately lobed, slightly dentate.
*Texture, upper surface.*—Bi-fid T-shaped hairs.
*Lower surface.*—Bi-fid T-shaped hairs.
*Color of veins, upper surface.*—RHS 146D.
*Color of veins, lower surface.*—RHS 146D.
*Petiole color.*—RHS 144B.
*Length.*—1-1.5 cm.
*Diameter.*—0.2-0.25 cm.
*Texture.*—Bi-fid T-shaped hairs.
Stem:
*Quantity of main branches per plant.*—3-4.
*Quantity of leaves per branch.*—8-12.
*Color of stem.*—Closest to RHS 144A.
*Length of stem.*—23-26 cm.
*Diameter.*—0.4 cm.
*Length of internodes.*—1.0-3.5 cm.
*Texture.*—Bi-fid T-shaped hairs.
*Color of peduncle.*—Closest to RHS 146B.
*Length of peduncle.*—4.7-5.2 cm.
*Peduncle diameter.*—0.2-0.25 cm.
*Texture.*—Bi-fid T-shaped hairs.
Inflorescence:
*Type.*—Composite type, solitary inflorescences (decorative-type) borne terminally above foliage, ray florets arranged acropetally on a capitulum.
*Quantity of short days to flowering (response time).*—50-55 days with center bud removal.
*Quantity of inflorescences per plant.*—6-10.
*Lastingness of individual blooms on the plant.*—About 30 days.
*Fragrance.*—Slight.
Bud (just before opening/showing color):
*Color.*—RHS 72A.
*Length.*—1.5-1.7 cm.
*Width.*—1.2-1.5 cm.
*Shape.*—Oblate.
Immature inflorescence:
*Diameter.*—2.5-3.0 cm.
*Color of ray florets, upper surface.*—About RHS 60B.
*Lower surface.*—About RHS 72A.
Mature inflorescence:
*Diameter.*—6.0-6.5 cm.
*Total diameter of 'disc'.*—1.0 cm.
Ray florets:
*Average quantity of florets.*—About 100-120.
*Color of florets, upper surface.*—RHS 75A to RHS 75B, fading to RHS N155B ground color overlaid very slightly with RHS 75D in vertical stripes.
*Lower surface.*—RHS 75C.
*Length.*—2.6-2.9 cm.
*Width.*—1.2-1.4 cm.
*Shape.*—Obovate.
*Apex shape.*—Rounded.
*Margin.*—Entire, rolled inward basally.
*Texture, upper surface.*—Papillose.
*Lower surface.*—Papillose.
Disc florets:
*Average quantity of florets.*—50-75.
*Color of florets.*—RHS 14A.
*Length.*—0.5 cm.
*Width.*—0.1 cm.
*Shape.*—Tubular, enlongated.
*Apex shape.*—Acute, 5 pointed.
Phyllaries:
*Quantity.*—16-20.
*Color, upper surface.*—RHS 137A.
*Lower surface.*—RHS 137A.
*Length.*—0.5-0.6 cm.
*Width.*—0.15-0.25 cm.
*Shape.*—Lanceolate.
*Apex shape.*—Acute.
*Based.*—Fused.
*Margins.*—Entire and papery.
*Texture, upper surface.*—Glossy and smooth.
*Lower surface.*—Bi-fid T-shaped hairs.
Reproductive organs:
*Pistil.*—1.
*Length.*—0.5 cm.
*Style color.*—RHS N144A but somewhat translucent.
*Style length.*—0.3-0.4 cm.
*Stigma color.*—RHS 17B.
*Stigma shape.*—Bi-parted.
*Ovary color.*—About RHS 155C.
*Stamens.*—4.
*Color of filaments.*—A little lighter than RHS N144A and somewhat translucent.
*Length filaments.*—0.3 cm.
*Anther color.*—RHS 15A.
*Anther length.*—0.1 cm.
*Anther shape.*—Oblong.
*Color of pollen.*—RHS 17A.
*Pollen amount.*—Moderate.
*Fertility/seed set.*—Has not been observed on this hybrid.
Disease/pest resistance: Disease resistance or susceptibility has not been observed on this hybrid.

What is claimed is:

1. A new and distinct variety of *Chrysanthemum* plant named 'Bold Yonew York,' substantially as illustrated and described herein.

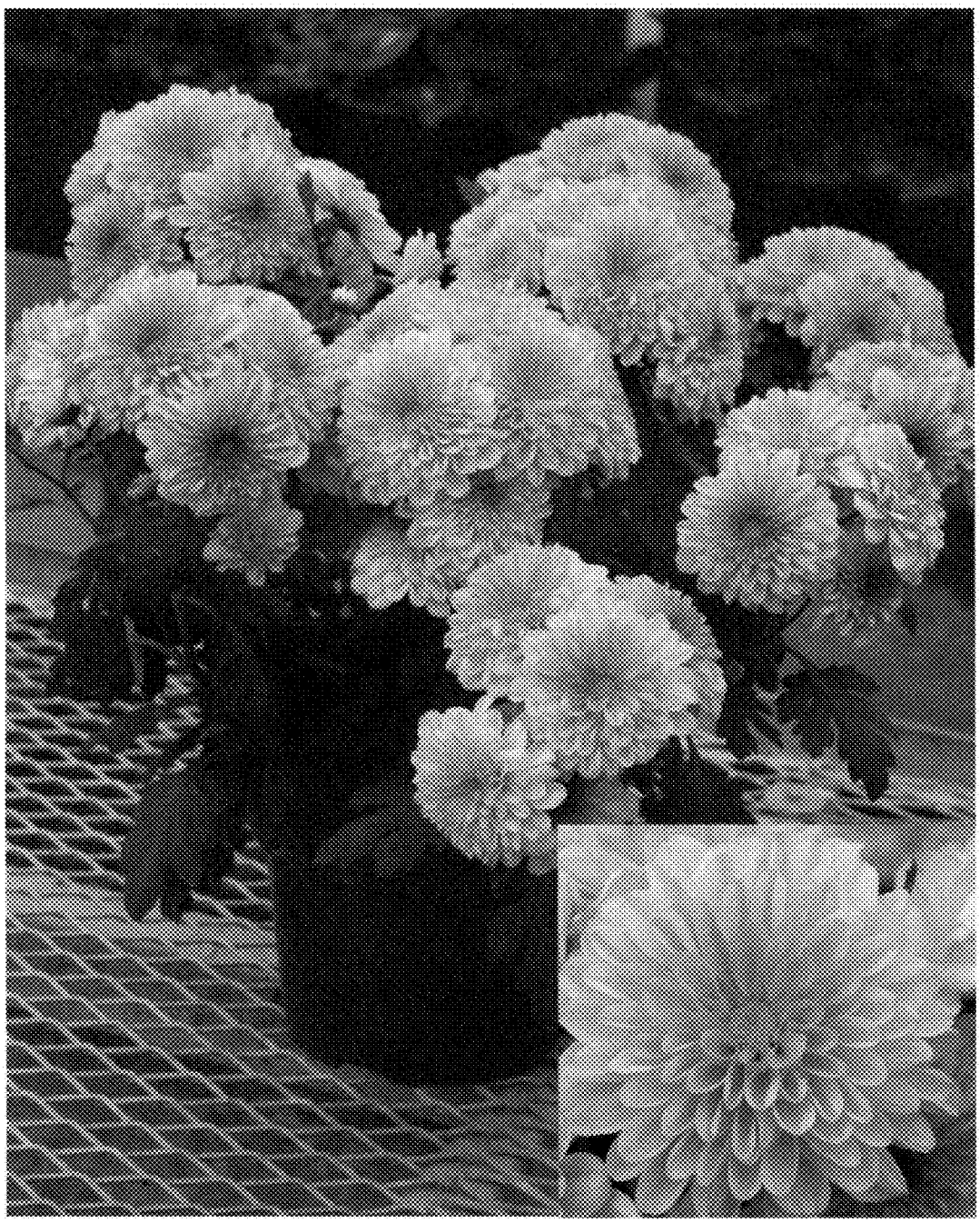

* * * * *